(12) United States Patent
Vad et al.

(10) Patent No.: US 10,271,974 B2
(45) Date of Patent: Apr. 30, 2019

(54) HELICAL STENT

(75) Inventors: Siddharth U. Vad, Bloomington, IN (US); Mark R. Frye, Bloomington, IN (US); Sean D. Chambers, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 13/530,685

(22) Filed: Jun. 22, 2012

(65) Prior Publication Data

US 2012/0330402 A1 Dec. 27, 2012

Related U.S. Application Data

(60) Provisional application No. 61/500,986, filed on Jun. 24, 2011.

(51) Int. Cl.
*A61F 2/88* (2006.01)
*A61F 2/07* (2013.01)
*A61F 2/89* (2013.01)

(52) U.S. Cl.
CPC ............... *A61F 2/88* (2013.01); *A61F 2/07* (2013.01); *A61F 2/89* (2013.01); *A61F 2220/0075* (2013.01); *A61F 2240/001* (2013.01)

(58) Field of Classification Search
CPC .... A61F 2/88; A61F 2/91; A61F 2/885; A61F 2/86; A61F 2/89; A61F 2/90; A61F 2/915
USPC ................. 623/1.22, 1.2, 1.11, 1.15
See application file for complete search history.

(56) References Cited

U.S. PATENT DOCUMENTS

| 4,561,439 | A | | 12/1985 | Bishop et al. |
| 4,886,062 | A | | 12/1989 | Wiktor |
| 5,019,090 | A | * | 5/1991 | Pinchuk ............... 623/1.15 |
| 5,226,913 | A | | 7/1993 | Pinchuk |
| 5,269,751 | A | | 12/1993 | Kaliman et al. |
| 5,282,824 | A | | 2/1994 | Gianturco |
| 5,314,472 | A | | 5/1994 | Fontaine |
| 5,316,023 | A | | 5/1994 | Palmaz et al. |
| 5,360,443 | A | | 11/1994 | Barone et al. |
| 5,370,653 | A | | 12/1994 | Cragg |
| 5,370,683 | A | | 12/1994 | Fontaine |
| 5,376,100 | A | | 12/1994 | Lefebvre |
| 5,443,498 | A | | 8/1995 | Fontaine |
| 5,476,506 | A | | 12/1995 | Lunn |

(Continued)

FOREIGN PATENT DOCUMENTS

| WO | WO 91/12779 A1 | 9/1991 |
| WO | WO 96/21404 A1 | 7/1996 |

(Continued)

OTHER PUBLICATIONS

International Search Report and Written Opinion of the International Searching Authority for International Application No. PCT/US2009/005005, dated Nov. 16, 2009, 10 pages.

(Continued)

*Primary Examiner* — Eric J Rosen
*Assistant Examiner* — Chima U Igboko
(74) *Attorney, Agent, or Firm* — Brinks Gilson & Lione

(57) ABSTRACT

A helical stent is provided that is wound in a zig-zag pattern along a pitch angle with respect to a plane transverse to the axis of the stent. A bisecting line extending through a bend and between two adjacent angular struts is also angled with respect to the longitudinal axis of the stent.

7 Claims, 2 Drawing Sheets

(56) References Cited

U.S. PATENT DOCUMENTS

| | | | |
|---|---|---|---|
| 5,507,767 A | 4/1996 | Maeda et al. | |
| 5,527,354 A | 6/1996 | Fontaine et al. | |
| 5,554,182 A | 9/1996 | Dinh et al. | |
| 5,575,818 A * | 11/1996 | Pinchuk | 623/1.15 |
| 5,591,195 A | 1/1997 | Taheri et al. | |
| D390,957 S | 2/1998 | Fontaine | |
| 5,782,904 A | 7/1998 | White et al. | |
| 5,800,456 A | 9/1998 | Maeda et al. | |
| 5,824,037 A * | 10/1998 | Fogarty | A61F 2/07 623/1.13 |
| 5,865,723 A | 2/1999 | Love | |
| 5,925,061 A * | 7/1999 | Ogi et al. | 623/1.2 |
| 5,968,057 A | 10/1999 | Taheri | |
| 5,984,965 A | 11/1999 | Knapp et al. | |
| 6,019,779 A | 2/2000 | Thorud et al. | |
| 6,042,605 A * | 3/2000 | Martin | A61F 2/07 623/1.13 |
| 6,077,296 A | 6/2000 | Shokoohi et al. | |
| 6,090,128 A | 7/2000 | Douglas | |
| 6,136,023 A * | 10/2000 | Boyle | 623/1.22 |
| 6,137,060 A | 10/2000 | Avellanet | |
| 6,156,062 A | 12/2000 | McGuiness | |
| 6,156,063 A | 12/2000 | Douglas | |
| 6,159,239 A | 12/2000 | Greenhalgh | |
| 6,187,036 B1 | 2/2001 | Shaolian et al. | |
| 6,191,365 B1 | 2/2001 | Avellanet | |
| 6,192,944 B1 * | 2/2001 | Greenhalgh | 139/425 R |
| 6,197,049 B1 | 3/2001 | Shaolian et al. | |
| 6,210,422 B1 | 4/2001 | Douglas | |
| 6,261,316 B1 | 7/2001 | Shaolian et al. | |
| 6,270,524 B1 | 8/2001 | Kim | |
| 6,278,057 B1 | 8/2001 | Avellanet | |
| 6,319,277 B1 | 11/2001 | Rudnick et al. | |
| 6,331,188 B1 * | 12/2001 | Lau et al. | 623/1.13 |
| 6,331,190 B1 | 12/2001 | Shokoohi et al. | |
| 6,338,739 B1 | 1/2002 | Datta et al. | |
| 6,361,637 B2 | 3/2002 | Martin et al. | |
| 6,364,904 B1 | 4/2002 | Smith | |
| 6,440,161 B1 | 8/2002 | Madrid et al. | |
| 6,454,775 B1 | 9/2002 | Demarais et al. | |
| 6,491,619 B1 | 12/2002 | Trauthen et al. | |
| 6,500,202 B1 | 12/2002 | Shaolian et al. | |
| 6,508,835 B1 | 1/2003 | Shaolian et al. | |
| 6,517,570 B1 | 2/2003 | Lau et al. | |
| 6,517,572 B2 | 2/2003 | Kugler et al. | |
| 6,520,986 B2 | 2/2003 | Martin et al. | |
| 6,530,935 B2 | 3/2003 | Wensel et al. | |
| 6,551,350 B1 | 4/2003 | Thornton et al. | |
| 6,565,596 B1 | 5/2003 | White et al. | |
| 6,635,080 B1 | 10/2003 | Lauterjung et al. | |
| 6,652,548 B2 | 11/2003 | Evans et al. | |
| 6,660,030 B2 | 12/2003 | Shaolian et al. | |
| 6,663,665 B2 | 12/2003 | Shaolian et al. | |
| D484,979 S | 1/2004 | Fontaine | |
| 6,685,618 B2 | 2/2004 | Tam et al. | |
| 6,685,696 B2 | 2/2004 | Fleischhacker et al. | |
| 6,685,722 B1 | 2/2004 | Rosenbluth et al. | |
| 6,685,736 B1 | 2/2004 | White et al. | |
| 6,689,157 B2 | 2/2004 | Madrid et al. | |
| 6,692,509 B2 | 2/2004 | Wensel et al. | |
| 6,699,170 B1 | 3/2004 | Crocker et al. | |
| 6,709,452 B1 * | 3/2004 | Valimaa et al. | 623/1.15 |
| 6,733,523 B2 | 5/2004 | Shaolian et al. | |
| 6,773,457 B2 | 8/2004 | Ivancev et al. | |
| 6,866,680 B2 | 3/2005 | Yassour et al. | |
| 6,923,828 B1 | 8/2005 | Wiktor | |
| 6,926,725 B2 | 8/2005 | Cooke et al. | |
| 6,929,709 B2 | 8/2005 | Smith | |
| 6,951,572 B1 | 10/2005 | Douglas | |
| 6,953,475 B2 | 10/2005 | Shaolian et al. | |
| 6,974,471 B2 | 12/2005 | Van Schie et al. | |
| 6,974,473 B2 | 12/2005 | Barclay et al. | |
| 6,986,784 B1 | 1/2006 | Weiser et al. | |
| 7,018,401 B1 | 3/2006 | Hyodoh et al. | |
| 7,037,316 B2 | 5/2006 | McGuckin, Jr. et al. | |
| 7,044,905 B2 | 5/2006 | Vidlund et al. | |
| 7,060,092 B2 | 6/2006 | Kuribayashi et al. | |
| 7,318,835 B2 | 1/2008 | Berra | |
| 8,366,765 B2 * | 2/2013 | Baldwin et al. | 623/1.22 |
| 2001/0007954 A1 | 7/2001 | Shaolian et al. | |
| 2002/0013617 A1 | 1/2002 | Matsutani et al. | |
| 2002/0156523 A1 | 10/2002 | Lau et al. | |
| 2002/0165603 A1 | 11/2002 | Thornton et al. | |
| 2003/0088305 A1 | 5/2003 | Van Schie et al. | |
| 2003/0130721 A1 | 7/2003 | Martin et al. | |
| 2003/0149475 A1 | 8/2003 | Hyodoh et al. | |
| 2004/0024443 A1 | 2/2004 | Dwyer et al. | |
| 2004/0044401 A1 | 3/2004 | Bales et al. | |
| 2004/0093072 A1 | 5/2004 | Pappas et al. | |
| 2004/0116960 A1 | 6/2004 | Demond et al. | |
| 2004/0117003 A1 | 6/2004 | Ouriel et al. | |
| 2005/0049574 A1 | 3/2005 | Petrick et al. | |
| 2005/0075715 A1 | 4/2005 | Borges et al. | |
| 2005/0085894 A1 | 4/2005 | Kershner | |
| 2005/0137677 A1 | 6/2005 | Rush | |
| 2005/0137680 A1 | 6/2005 | Ortiz et al. | |
| 2005/0154448 A1 | 7/2005 | Cully et al. | |
| 2005/0177246 A1 | 8/2005 | Datta et al. | |
| 2005/0246010 A1 * | 11/2005 | Alexander et al. | 623/1.12 |
| 2006/0004436 A1 | 1/2006 | Amarant et al. | |
| 2006/0030926 A1 | 2/2006 | Berra | |
| 2006/0129222 A1 * | 6/2006 | Stinson | 623/1.2 |
| 2006/0142841 A1 | 6/2006 | Khosravi et al. | |
| 2006/0149358 A1 * | 7/2006 | Zilla et al. | 623/1.22 |
| 2006/0265052 A1 | 11/2006 | You | |
| 2006/0293744 A1 | 12/2006 | Peckham et al. | |
| 2007/0067024 A1 | 3/2007 | White et al. | |
| 2007/0112412 A1 | 5/2007 | Shokoohi et al. | |
| 2007/0198079 A1 | 8/2007 | Casey, II et al. | |
| 2007/0207186 A1 | 9/2007 | Scanlon et al. | |
| 2007/0208409 A1 * | 9/2007 | Quigley | 623/1.13 |
| 2007/0208421 A1 | 9/2007 | Quigley | |
| 2007/0215268 A1 | 9/2007 | Pingleton et al. | |
| 2007/0219618 A1 * | 9/2007 | Cully et al. | 623/1.13 |
| 2007/0299497 A1 | 12/2007 | Shaolian et al. | |
| 2008/0082154 A1 | 4/2008 | Tseng et al. | |
| 2008/0082158 A1 | 4/2008 | Tseng et al. | |
| 2008/0082159 A1 * | 4/2008 | Tseng et al. | 623/1.13 |
| 2008/0114445 A1 | 5/2008 | Melsheimer et al. | |
| 2008/0147172 A1 | 6/2008 | White et al. | |
| 2008/0195191 A1 | 8/2008 | Luo et al. | |
| 2008/0221664 A1 * | 9/2008 | Bales et al. | 623/1.22 |
| 2008/0228262 A1 | 9/2008 | Goldmann et al. | |
| 2008/0262594 A1 | 10/2008 | Morris | |
| 2008/0319529 A1 | 12/2008 | Krivoruchko et al. | |
| 2008/0319534 A1 * | 12/2008 | Birdsall et al. | 623/1.22 |
| 2008/0319535 A1 | 12/2008 | Craven et al. | |
| 2009/0030499 A1 | 1/2009 | Bebb et al. | |
| 2009/0054972 A1 | 2/2009 | Norton et al. | 623/1.53 |
| 2009/0177268 A1 * | 7/2009 | Lundkvist et al. | 623/1.22 |
| 2009/0259294 A1 * | 10/2009 | Cully et al. | 623/1.22 |
| 2009/0264982 A1 * | 10/2009 | Krause et al. | 623/1.15 |
| 2009/0306766 A1 * | 12/2009 | McDermott et al. | 623/1.16 |
| 2010/0004725 A1 * | 1/2010 | Zipse et al. | 623/1.2 |
| 2010/0049296 A1 * | 2/2010 | Sarasam et al. | 623/1.11 |
| 2010/0070024 A1 * | 3/2010 | Venturelli et al. | 623/1.22 |
| 2010/0076543 A1 * | 3/2010 | Melsheimer et al. | 623/1.13 |
| 2010/0152837 A1 * | 6/2010 | Lundkvist et al. | 623/1.22 |
| 2010/0198333 A1 * | 8/2010 | Macatangay et al. | 623/1.15 |
| 2011/0009951 A1 | 1/2011 | Bogert | |
| 2011/0071613 A1 | 3/2011 | Wood | |
| 2011/0087318 A1 * | 4/2011 | Daugherty et al. | 623/1.13 |

FOREIGN PATENT DOCUMENTS

| | | |
|---|---|---|
| WO | WO 98/27894 A1 | 7/1998 |
| WO | WO 99/37242 A1 | 7/1999 |
| WO | WO 99/44536 A1 | 9/1999 |
| WO | WO 00/28922 A1 | 5/2000 |
| WO | WO 01/52770 A1 | 7/2001 |
| WO | WO 01/52771 A1 | 7/2001 |
| WO | WO 03/057079 A1 | 7/2003 |

(56) References Cited

FOREIGN PATENT DOCUMENTS

| | | |
|---|---|---|
| WO | WO 2004/073557 A2 | 9/2004 |
| WO | WO 2009/058369 A1 | 5/2009 |
| WO | WO 2011/034795 A1 | 3/2011 |

OTHER PUBLICATIONS

International Preliminary Report on Patentability, PCT/US2010/022515, dated May 6, 2011, 10 pages.
Extended European Search Report for Eurpoean Application No. 16150460.0, dated Mar. 29, 2016, 10 pages.
Examination Report for corresponding EP Application No. 16150460.0 dated Apr. 19, 2017, 6 pages.

* cited by examiner

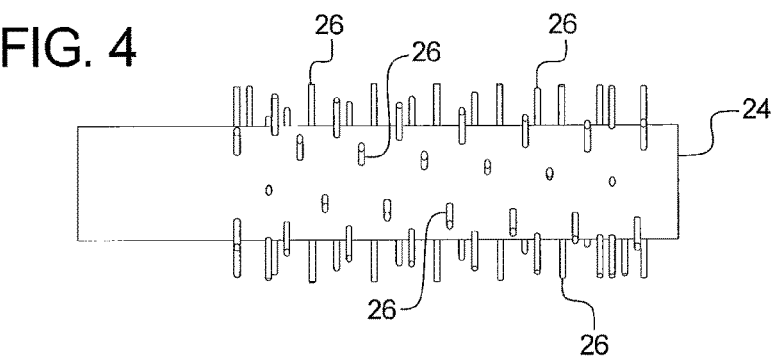
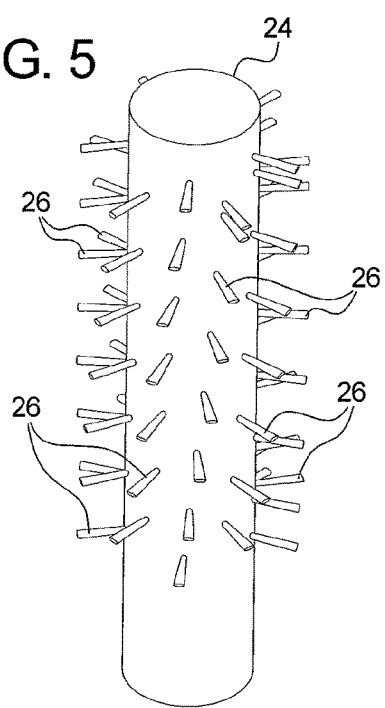
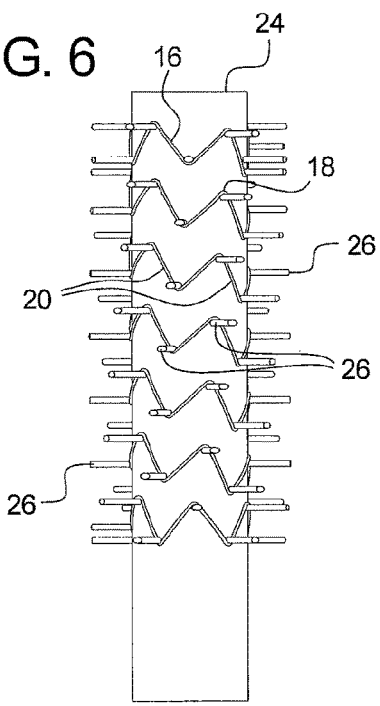
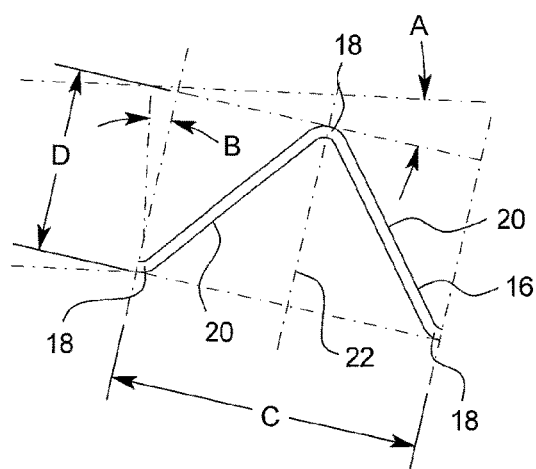

HELICAL STENT

This application claims priority to U.S. Provisional Application No. 61/500,986, filed Jun. 24, 2011, which is hereby incorporated by reference herein.

BACKGROUND

The present invention relates generally to medical devices and more particularly to a stent structure.

Stents have become relatively common devices for treating a number of organs, such as the vascular system, colon, biliary tract, urinary tract, esophagus, trachea and the like. Stents are useful in treating various ailments including blockages, occlusions, narrowing conditions and other related problems that restrict flow through a passageway (generally referred to as a stenosis). Stents are also useful in a variety of other medical procedures including treating various types of aneurysms.

For example, stents may be used to treat numerous vessels in the vascular system, including coronary arteries, peripheral arteries (e.g., carotid, brachial, renal, iliac and femoral), and other vessels. Stents have become a common alternative for treating vascular conditions because stenting procedures are considerably less invasive than other alternatives. As an example, stenoses in the coronary arteries have traditionally been treated with bypass surgery. In general, bypass surgery involves splitting the chest bone to open the chest cavity and grafting a replacement vessel onto the heart to bypass the stenosed artery. However, coronary bypass surgery is a very invasive procedure that is risky and requires a long recovery time for the patient. By contrast, stenting procedures are performed transluminally and do not require open surgery. In fact, open surgery has been shown to be unsuitable in patients with significant comorbities due to a high risk of mortality, morbidity, and trauma associated with this procedure. Thus, stenting reduces recovery time and the risks associated with surgery are minimized.

Many different types of stents and stenting procedures are possible. In general, however, stents are typically designed as tubular support structures that may be inserted percutaneously and translumimally through a body passageway. Typically, stents are made from a structure that wraps around at least a portion of a circumference and are adapted to compress and expand between a smaller and larger diameter. Stents may be self-expanding so that they elastically expand out to a preset larger diameter, or may be balloon-expandable in which the stent is deployed by applying a high pressure to the stent inner surface by a balloon. However, other types of stents are designed to have a fixed diameter and are not generally compressible. Although stents may be made from many types of materials, including non-metallic materials and natural tissues, common examples of metallic materials that may be used to make stents include stainless steel and nitinol. Other materials may also be used, such as cobalt-chrome alloys, amorphous metals, tantalum, platinum, gold, titanium, polymers and/or compatible tissues. Typically, stents are implanted within an artery or other passageway by positioning the stent within the lumen to be treated and then expanding the stent from a compressed diameter to an expanded diameter. The ability of the stent to expand from a compressed diameter makes it possible to navigate the stent through narrow, tortuous passageways to the area to be treated while the stent is in a relatively small, compressed diameter. Once the stent has been positioned and expanded at the area to be treated, the tubular support structure of the stent contacts and radially supports the inner wall of the passageway. The implanted stent may be used to mechanically prevent the passageway from closing in order to keep the passageway open to facilitate fluid flow through the passageway. Conversely, stents may also be used to support a graft layer to prevent fluid flow through the side walls of the stent. However, these are only some of the examples of how stents may be used, and stents may be used for other purposes as well.

Self-expanding stents are one common type of stent used in medical procedures. Self-expanding stents are increasingly being used by physicians because of their adaptability to a variety of different conditions and procedures. Self-expanding stents are usually made of shape memory materials or other elastic materials that act like a spring. Typical metals used in this type of stent include nitinol and 304 stainless steel. However, other materials may also be used. To facilitate stent implantation, self-expanding stents are normally installed on the end of a catheter in a low profile, compressed state. The stent is typically retained in the compressed state by inserting the stent into a sheath at the end of the catheter. The stent is then guided to the portion of the vessel to be treated. Once the catheter and stent are positioned adjacent the portion to be treated, the stent is released by pulling, or withdrawing, the sheath rearward. Normally, a step or other feature is provided on the catheter to prevent the stent from moving rearward with the sheath. After the stent is released from the retaining sheath, the stent springs radially outward to an expanded diameter until the stent contacts and presses against the vessel wall. Traditionally, self-expanding stents have been used in areas where the vasculature experiences a variety of motion, trauma and tortuousity. One common area of use for self-expanding stents is peripheral arteries in the vascular system. One advantage of self-expanding stents for peripheral arteries is that traumas from external sources do not permanently deform the stent. As a result, the stent may temporarily deform during unusually harsh traumas and spring back to its expanded state once the trauma is relieved. However, self-expanding stents may be used in many other applications as well.

Balloon-expandable stents are often used to treat stenosis of the coronary arteries but may be used in other treatments as well. Usually, balloon-expandable stents are made from ductile materials that plastically deform relatively easily. In the case of stents made from metal, 316L stainless steel that has been annealed is a common choice for this type of stent. One procedure for implanting balloon-expandable stents involves mounting the stent circumferentially on the balloon of a balloon-tipped catheter and threading the catheter over a guidewire through a vessel passageway to the area to be treated. Once the balloon is positioned at the narrowed portion of the vessel to be treated, the balloon is expanded by pumping saline through the catheter to the balloon. As a result, the balloon simultaneously dilates the vessel and radially expands the stent within the dilated portion. The balloon is then deflated and the balloon-tipped catheter is retracted from the passageway. This leaves the expanded stent permanently implanted at the desired location. Ductile metal lends itself to this type of stent since the stent may be compressed by plastic deformation to a small diameter when mounted onto the balloon. When the balloon is later expanded in the vessel, the stent is once again plastically deformed to a larger diameter to provide the desired radial support structure. Traditionally, balloon-expandable stents have been more commonly used in coronary vessels than in peripheral vessels because of the deformable nature of these stents. One reason for this is that balloon-expandable stents can be precisely sized to a particular vessel diameter and shape since the ductile metal that is used can be plastically deformed to a desired size and shape. In addition, there is minimal risk that a coronary vessel will experience a trauma from an external source that would permanently deform a balloon-expandable stent.

Stents may also be used in combination with other components to treat a number of medical conditions. For example, stent-graft assemblies are commonly used in the treatment of aneurysms. As those in the art well know, an aneurysm is an abnormal widening or ballooning of a portion of an artery. Generally, this condition is caused by a weakness in the blood vessel wall. High blood pressure and atherosclerotic disease may also contribute to the formation of aneurysms. Common types of aneurysms include aortic aneurysms, cerebral aneurysms, popliteal artery aneurysms, mesenteric artery aneurysms, and splenic artery aneurysms. However, it is also possible for aneurysms to form in blood vessels throughout the vasculature. If not treated, an aneurysm may eventually rupture, resulting in internal hemorrhaging. In many cases, the internal bleeding may be so massive that a patient can die within minutes of an aneurysm rupture. For example, in the case of aortic aneurysms, the survival rate after a rupture can be as low as 20%.

Traditionally, aneurysms have been treated with surgery. For example, in the case of an abdominal aortic aneurysm, the abdomen is surgically opened, and the widened section of the aorta is typically dissected longitudinally. A graft material, such as Dacron, is then inserted into the vessel and sutured at each end to the inner wall of the non-widened portions of the vessel. The dissected edges of the vessel may then be overlapped and sutured to enclose the graft material within the vessel. In smaller vessels where the aneurysm forms a balloon-like bulge with a narrow neck connecting the aneurysm to the vessel, the surgeon may put a clip on the blood vessel wall at the neck of the aneurysm between the aneurysm and the primary passageway of the vessel. The clip then prevents blood flow from the vessel from entering the aneurysm.

An alternative to traditional surgery is endovascular treatment of the blood vessel with a stent-graft. This alternative involves implanting a stent-graft in the blood vessel across the aneurysm using conventional catheter-based placement techniques. The stent-graft treats the aneurysm by sealing the wall of the blood vessel with a generally impermeable graft material. Thus, the aneurysm is sealed off and blood flow is kept within the primary passageway of the blood vessel. Increasingly, treatments using stent-grafts are becoming preferred since the procedure results in less trauma and a faster recuperation.

SUMMARY

A stent is described that is helical in two different aspects. The stent is made from a wire that is configured with a series of bends and angular struts. A pattern of bends and struts is defined by a pitch angle with respect to a plane transverse to the axis of the stent. The bends and struts also define a bisecting line that extends through a bend and between two circumferentially adjacent angular struts. The bisecting line is angled with respect to the longitudinal axis of the stent. The inventions herein may also include any other aspect described below in the written description or in the attached drawings and any combinations thereof.

BRIEF DESCRIPTION OF SEVERAL VIEWS OF THE DRAWINGS

The invention may be more fully understood by reading the following description in conjunction with the drawings, in which:

FIG. 4 is a side view of a mandrel;
FIG. 5 is a perspective view of the mandrel;
FIG. 6 is a side view of the mandrel with a wire wrapped around the mandrel;
and
FIG. 7 is an enlarged view of the wire pattern of the stent.

DETAILED DESCRIPTION

Figure 1:
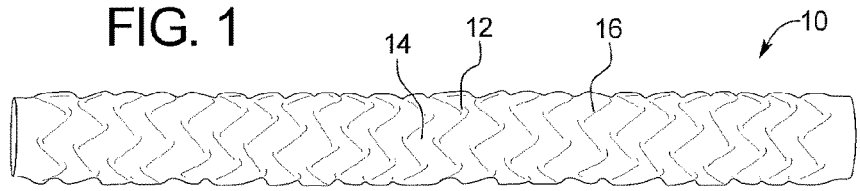
FIG. 1 is a side view of a stent-graft.
Figure 2:
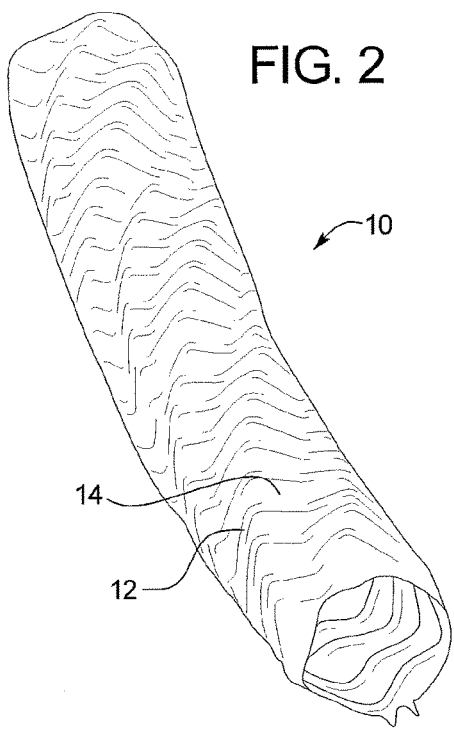
FIG. 2 is an end perspective view of the stent-graft.
Figure 3:
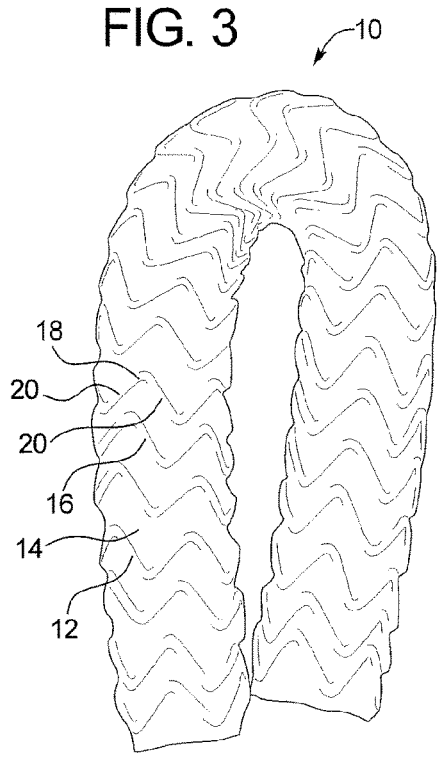
FIG. 3 is a side view of the stent-graft, showing the stent-graft bent.

Referring now to the figures, and particularly to FIGS. 1-3, a stent-graft 10 is shown for intraluminal medical treatments. The stent-graft 10 includes a stent 12 and a graft layer 14 adhered to the stent 12. The graft layer 14 may be made of various materials and adhered to the stent 12 in various ways. For example, the graft layer 14 may be made from Thoralon, ultra high molecular weight polyethylene, ePTFE, PET, collagen materials, polyurethanes, woven materials, or other suitable graft materials. The graft layer 14 may be attached to the stent 12 by the use of sutures, dip coating, spraying, electro-spinning, or other suitable techniques.

The stent 12 is preferably formed by a single wire 16 that is wound around the stent 12 body in a helical cylindrical pattern. The wire 16 may be a round cross-sectional wire 16 that is wound around a cylindrical mandrel 24 as described below. Alternatively, the wire 16 may have a rectangular cross-section that is formed by laser cutting the wire 16 structure from a cannula. The wire 16 may also be a wire ribbon having a rectangular cross-section. Preferably, the wire 16 is made from an elastic material so that the stent 12 is self-expanding; however, a more ductile material could be used so that the stent 12 is balloon-expandable. For example, elastic materials that may be used include nitinol and stainless steel. The wire 16 may also be draw filled tubing where a tube of one material surrounds a core of another material. For instance, the core may be made from a radiopaque material to make the stent 12 visible using external visualization equipment without the need for separate radiopaque markers. The outer tube of the draw filled tubing may also be made from nitinol in order to make the stent 12 self-expanding. In addition, various forms of nitinol may be used, such as quaternary nitinol where tungsten, barium or erbium is added to conventional nitinol to increase radiopacity and chromium or cobalt is added to improve radial stiffness.

As shown in FIGS. 1 and 6, the wire 16 is bent back-and-forth along a helical pattern so that the wire 16 forms a series of bends 18 connecting circumferentially adjacent angular struts 20. Preferably, the wire 16 is in a stress relaxed state in the helically wound cylindrical pattern, which may be achieved by heat setting the stent 12 pattern as described below. The length of each of the angular struts 20 is equal to each other so that, as shown in FIG. 7, circumferentially adjacent angular struts 20 are the same length. Thus, the stent 12 structure is unlike some prior art stent structures where the strut lengths are unequal to give the stent a staggered pattern. However, the stent 12 pattern may include angular struts 20 with unequal lengths at the ends of the stent 12 to permit the ends of the stent 12 to form circular, non-helical rings.

As shown in FIG. 7, the helically wound pattern of bends 18 and struts 20 is defined by a pitch angle A with respect to a plane transverse to the axis of the stent 12. Preferably, the pitch angle A is from about 5° to about 20°. More preferably, the pitch angle A is from about 5° to about 15°. Most preferably, the pitch angle A is about 10°.

As also shown in FIG. 7, an imaginary bisecting line 22 extends through each bend 18 connecting two circumferentially adjacent angular struts 20 and between the circumferentially adjacent struts 20. Preferably, the bisecting line 22 is angled B from the longitudinal axis of the helically wound cylindrical pattern of the stent 12 from about 5° to about 20°. More preferably, the bisecting line 22 is angled B from about 5° to about 15°. Most preferably, the bisecting line 22 is angled B about 10°. However, it is preferable for angle A and angle B to be equal to each other.

Although the dimensions of the struts 20 and bends 18 may be varied, it is preferred that the width C of two circumferentially adjacent angular struts 20 be about 5.041 mm, and the height D of the angular struts 20 be about 3 mm from the outside of two opposing bends 18. The wire 16 preferably has a diameter of about 0.007", and the inner radius of the bends 18 is preferably about 0.008". These dimensions may be particularly suited to a stent with an 8 mm expanded diameter. However, the dimensions of the struts and bends may be designed to provide the desired radial force within the engineering strain limits of the material used so that the stent has the necessary fatigue resistance. For example, the value of C would depend upon the stent diameter and the number of peaks and valleys incorporated in one helical revolution. Most preferably, the number of peaks is about 5 to about 12, although more peaks may be incorporated to reduce the radial force or increase the fatigue resistance of the stent structure.

As shown in FIGS. 4-6, the stent 12 may be made by winding the wire 16 around a mandrel 24 with a circular cross-section. The mandrel 24 may have a series of pins 26 that extend radially outward from the mandrel 24. As shown in FIG. 6, the helically wound cylindrical stent 12 pattern may then be formed by bending the wire 16 around the pins 26 and around the mandrel 24. After the wire 16 has been fully bent around the pins 26 and wound around the mandrel 24, the wire 16 may be heat set while it remains on the mandrel 24 so that the wire 16 retains the helically wound cylindrical pattern as the relaxed state of the wire 16. The wire 16 may then be removed from the mandrel 24 and a graft layer 14 may be attached to the stent 12 as described above.

The helical stent 12 may have several advantages. As shown in FIGS. 1-2 and 5-6, the stent 12 is helically wound into different respects. First, the zig-zag pattern of bends 18 and struts 20 wraps helically around the circumference of the stent 12 so that the wire 16 forms continuously connected rings along the length of the stent 12. Second, longitudinally adjacent bends 18 are nested within each other but are circumferentially offset from each other so that the bends 18 are helically arranged relative to each other. Because the stent 12 does not have longitudinal connectors connecting adjacent rings, the stent 12 may be extremely flexible. In addition, as shown in FIG. 3, the stent 12 may have a high kink resistance, which may allow the stent 12 to be bent as much as 180° without kinking. The stent 12 also has a high proportion of open area through the stent 12 wall, which may be desirable for flexibility, fatigue and decreased vessel wall contact. The stent 12 may also have increased axial flexibility, which may permit the stent 12 to change length as much as 50% or more to accommodate shape changes in the vessel as a person moves his/her body. The helical pattern of the wire 16 may also impart a swirling motion to blood flowing through the stent 12, which may improve blood flow through the stent 12. The delivery profile of the stent 12 may also be improved, since angular struts 20 disposed diametrically opposite of each other may not be directly aligned with each other, which may permit the struts 20 to diametrically nest into each other to provide a lower profile compressed state.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:
1. A self-expanding stent graft, comprising:
   a tubular graft having a proximal end, a distal end, and a length from the proximal end to the distal end;
   a single elastic helical wire disposed on the graft and having first and second ends, the single elastic helical wire comprising a zig zag pattern of angular struts and bends connecting circumferentially adjacent angular struts, wherein the single elastic helical wire is preformed and set into a continuous helical cylindrical pattern prior to attachment to the tubular graft to comprise a tubular stent in a stressed relaxed state, and wherein the tubular stent is disposed along the length of the tubular graft and in the stress relaxed state;
   wherein all of the angular struts are of the same length;
   wherein longitudinally adjacent turns of the stent are free of any longitudinal connectors between them;
   wherein circumferentially adjacent bends define a pitch angle of the helical cylindrical pattern with respect to a plane transverse to the axis of the stent;
   wherein the bends and the angular struts define bisecting lines extending through the bends and between circumferentially adjacent angular struts, and the bisecting lines are angled from about 5° to about 20° with respect to a longitudinal axis extending through the helical cylindrical pattern of the stent,
   wherein longitudinally adjacent angular struts and bends are spaced apart from each other in the wire's relaxed state;
   wherein the stent is configured to change in length as much as 50% to accommodate shape changes in a patient's body;
   and
   wherein the stent graft is configured to bend one hundred and eighty degrees without kinking.

2. The stent graft of claim 1, wherein the ends of the single wire are formed into circular, non-helical rings having a zig zag pattern of struts and bends, wherein the struts in the circular, non-helical rings are of unequal lengths.

3. The stent graft of claim 1, wherein the pitch angle is from about 5° to about 20°.

4. The stent graft of claim 3, wherein the pitch angle and the angle of the bisecting lines is the same.

5. The stent graft of claim 4, wherein longitudinally adjacent bends are circumferentially offset from each other so that the bends are helically arranged relative to each other.

6. The stent graft of claim 5 wherein longitudinally adjacent bends are nested within each other.

7. The stent graft of claim 4 wherein longitudinally adjacent bends are nested within each other.

\* \* \* \* \*